United States Patent [19]

Hennecke et al.

[11] Patent Number: 5,536,652
[45] Date of Patent: Jul. 16, 1996

[54] L-PHENYLALANYL-TRNA SYNTHETASE MUTANTS, A PROCESS FOR THE PREPARATION THEREOF AND THE USE THEREOF FOR THE IN VIVO INCORPORATION OF NON-PROTEINOGENOUS AMINO ACIDS INTO PEPTIDES OR PROTEINS

[75] Inventors: Hauke Hennecke, Zürich; Peter Kast, Wetzikon, both of Switzerland

[73] Assignee: Hoechst Aktiengesellschaft, Frankfurt am Main, Germany

[21] Appl. No.: 286,262

[22] Filed: Aug. 5, 1994

Related U.S. Application Data

[62] Division of Ser. No. 822,275, Jan. 21, 1992, Pat. No. 5,370,995.

[30]     Foreign Application Priority Data

Dec. 18, 1991  [DE]  Germany ............................ 9115660 U

[51] Int. Cl.⁶ ............................... C12N 9/10; C12N 1/13; C12N 15/54; C12N 15/63
[52] U.S. Cl. .................... 435/172.3; 435/193; 435/317.1
[58] Field of Search .................................. 435/68.1, 69.1, 435/69.7, 172.3, 193, 317.1, 320.1, 91.3

[56]         References Cited

PUBLICATIONS

3P. Kast et al., "Amino Acid Substrate Specificity of *Escherichia coli* Phenylalanyl–tRNA Synthetase Altered by Distinct Mutations," J. Mol. Biol. 222:99–124 (1991).

Dissertation ETH Nr. 9468, "Investigations on *Escherichia coli* Phenylalanyl tRNA Synthetase at the Molecular Level: Identification and Genetic Engineering of a Phenylalanine Specificity Determinant and Possible Application of a Relaxed Specificity Mutant," presented by Peter Kast to Swiss Federal Institute of Technology Zurich (1991).

*Primary Examiner*—Dian C. Jacobson
*Attorney, Agent, or Firm*—Finnegan, Henderson, Farabow, Garrett & Dunner

[57]         ABSTRACT

L-Phenylalanyl-tRNA synthetase mutants, a process for the preparation thereof and the use thereof for the in vivo incorporation of non-proteinogenous amino acids into peptides or proteins.

The invention relates to L-phenylalanyl-tRNA synthetases from microorganisms which, by reason of a modification generated by genetic engineering, have an altered substrate selectivity, and to their preparation and use for the in vivo incorporation of non-proteinogenous amino acids into peptides or proteins.

4 Claims, No Drawings

SEQUENCE LISTING ( 1 ) GENERAL INFORMATION:

( i i i ) NUMBER OF SEQUENCES: 13

( 2 ) INFORMATION FOR SEQ ID NO:1:

(i) SEQUENCE CHARACTERISTICS:
    (A) LENGTH: 7 amino acids
    (B) TYPE: amino acid
    (D) TOPOLOGY: linear (ii) MOLECULE TYPE: peptide (xi) SEQUENCE DESCRIPTION: SEQ ID NO:1:

Gly Phe Ala Phe Gly Met Gly
1               5

(2) INFORMATION FOR SEQ ID NO:2:

(i) SEQUENCE CHARACTERISTICS:
    (A) LENGTH: 7 amino acids
    (B) TYPE: amino acid
    (D) TOPOLOGY: linear (ii) MOLECULE TYPE: peptide (xi) SEQUENCE DESCRIPTION: SEQ ID NO:2:

Gly Trp Ala Phe Gly Met Gly
1               5

(2) INFORMATION FOR SEQ ID NO:3:

(i) SEQUENCE CHARACTERISTICS:
    (A) LENGTH: 7 amino acids
    (B) TYPE: amino acid
    (D) TOPOLOGY: linear (ii) MOLECULE TYPE: peptide (xi) SEQUENCE DESCRIPTION: SEQ ID NO:3:

Gly Phe Ala Phe Gly Leu Gly
1               5

(2) INFORMATION FOR SEQ ID NO:4:

(i) SEQUENCE CHARACTERISTICS:
    (A) LENGTH: 7 amino acids
    (B) TYPE: amino acid
    (D) TOPOLOGY: linear (ii) MOLECULE TYPE: peptide (xi) SEQUENCE DESCRIPTION: SEQ ID NO:4:

Gly Trp Ala Phe Gly Leu Gly
1               5

(2) INFORMATION FOR SEQ ID NO:5:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:5:

CTGGTTTCGG NTTCGGGATG                                                                            20

(2) INFORMATION FOR SEQ ID NO:6:

(i) SEQUENCE CHARACTERISTICS:
    (A) LENGTH: 20 base pairs
    (B) TYPE: nucleic acid
    (C) STRANDEDNESS: single (D) TOPOLOGY: linear (ii) MOLECULE TYPE: DNA (genomic)

(xi) SEQUENCE DESCRIPTION: SEQ ID NO:6:

CTGGCTTCGG NTTTGGTATG                                                                                              20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AGGGCTTCGG NTTCGGAATG                                                                                              20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ACGGCTTCGG NTTCGGGCTC                                                                                              20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TTGGGTGGGG NTTTGGCTTG                                                                                              20

(2) INFORMATION FOR SEQ ID NO:10:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GACCCCGGGA CCAAAATGGC AAGTAAAATA GCCTGATGGG ATAGGCTC                                                                48

(2) INFORMATION FOR SEQ ID NO:11:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
TTAGAGCCTA TCCCATCAGG CTATTTACT TGCCATTTTG GTCCCGGGGT C                    51
```

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
CTGGTTTCGG CTTCGGGATG                                                       20
```

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
GCAGATTCGC TTCCG                                                            15
```

L-PHENYLALANYL-TRNA SYNTHETASE MUTANTS, A PROCESS FOR THE PREPARATION THEREOF AND THE USE THEREOF FOR THE IN VIVO INCORPORATION OF NON-PROTEINOGENOUS AMINO ACIDS INTO PEPTIDES OR PROTEINS

This is a division of application Ser. No. 07/822,275, filed Jan. 21, 1992, now U.S. Pat. No. 5,370,995.

The invention relates to L-phenylalanyl-tRNA synthetases from microorganisms which, by reason of a modification generated by genetic engineering, have an altered substrate selectivity, and to their preparation and use for the in vivo incorporation of non-proteinogenous amino acids into peptides or proteins.

The subject-matter of the invention was published on Jul. 22, 1991, in the form of the thesis of Dr. Peter Kast (Investigations on Escherichia coli Phenylalanyl-tRNA Synthetase at the Molecular 3Level: Identification and Genetic Engineering of a Phenylalanine Specificity Determinant and Possible Application of a Relaxed Specificity Mutant; ETH Thesis No. 9468, ETH Zurich, 1991 and P. Kast et al. (1991) J Mol Biol 222, pages 99–124).

L-Phenylalanyl-tRNA synthetase (E) catalyzes the following reaction steps:

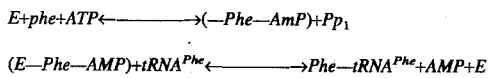

L-Phenylalanyl-tRNA synthetase from E. coli K12 has the quaternary structure $\alpha_2\beta_2$. Investigations to date have revealed that tRNA$^{Phe}$ binding sites are located on the large $\beta$ subunit of the enzyme and that L-phenylalanine and ATP binding determinants are presumably located on the small $\alpha$ subunit. The catalytically active center is probably located at a contact point of these subunits.

The amino-acid sequences of the $\alpha$ subunits of L-phenylalanyl-tRNA synthetases from E. coli K12, Salmonella typhimurium, Bacillus subtilis, Thermus thermophilus and Saccharomyces cerevisiae (mitochondria) have a relatively great similarity of sequences at the C-terminal end.

By contrast, the similarity in amino acids of the $\alpha$ subunit of the enzyme from the yeast cytoplasm with the $\alpha$ subunit of the enzymes from E. coli K12 and the above-mentioned microorganisms is distinctly less pronounced. Thus, for example, a glycine residue is located at amino acid position 458 of the enzyme from the cytoplasm of the yeast, whereas an alanine residue is present in each case at the corresponding position of the enzyme from yeast mitochondria or bacterial L-phenylalanyl-tRNA synthetases (for example in position 294 of the $\alpha$ subunit of the enzyme from E. coli K12).

It is also known that the known L-phenylalanyl-tRNA synthetase from E. coli K12 and from the cytoplasm of the yeast transfers not only the natural L-phenylalanine but also the unnatural amino acid p-F-L-phenylalanine. However, the transfer of this non-proteinogenous amino acid takes place distinctly less efficiently than that of the natural L-phenylalanine [H. J. Gabius et al (1983), Biochemistry, 22, 2331–2339 and Peter Kast, ETH Zürich, ETH Thesis No. 9468, 1991]. The transfer of other L-phenylalanine residues halogenated in the para position or derivatives thereof has not been observed to date.

The operon encoding L-phenylalanyl-tRNA synthetase has already been isolated from E. coli K12. The relevant $\alpha$ and $\beta$ subunits of the enzyme are encoded by the genes pheS and pheT. DNA sequence analysis of the pheS gene of E. coli K12 within the scope of this invention revealed a CGT (L-arginine) codon at nucleotide positions 220 to 222 in place of a GCT (L-alanine) codon in contra-distinction to the data published by G. Fayat et al. (1983, J Mol Biol 171, 239–261).

The incorporation of non-proteinogenous amino acids into proteins or peptide active substances, such as, for example, the in vitro incorporation of p-F-L-phenylalanine into angiotensin II or bradykinin (W. H. Vine et al., 1973, Biochemistry 12, 1630–1637), the in vivo incorporation of L-2-aminohexanoic acid into human epidermal growth factor (H. Koide et al., 1988, Proc Natl Acad Sci USA, 1988, 85, 6237–6241) or into other proteins may alter their properties, such as, for example, their biological activity, toxicity, stability, solubility or absorbability, and protect them from proteolytic degradation.

Available to date for the in vivo incorporation of non-proteinogenous amino acids into proteins or peptide active substances have been merely unaltered, i.e. natural aminoacyl-tRNA synthetases from microorganisms, which are generally distinguished by a high substrate specificity and which therefore accept non-proteinogenous amino acids as substrate only poorly or not at all.

It has now been found, surprisingly, that replacement of the conserved alanine residue (*) by a glycine residue in the C-terminal amino-acid sequence (SEQ. ID NOS: 1–4): Gly, Phe|Trp, Ala*, Phe, Gly, Met|Leu, Gly in the $\alpha$ subunit of the L-phenyl-alanyl-tRNA synthetase from E. coli K12, Salmonella typhimurium, Thermus thermophilus, Bacillus subtilis and yeast mitochondria (Saccharomyces cerevisiae) results in a widening of the substrate selectivity of the L-phenylalanyl-tRNA synthetase.

The invention thus relates to:

1. A L-phenylalanyl-tRNA Synthetase whose conserved alanine residue (*) in the sequence Gly, Phe|Trp, Ala*, Phe, Gly, Met|Leu, Gly (SEQ. ID NOS: 1–4) is altered to glycine by a modification at the DNA level;

2. A DNA or RNA sequence coding for the L-phenylalanyl-tRNA synthetase mentioned under 1.;

3. Cells or microorganisms which contain the L-phenylalanyl-tRNA synthetase mentioned under 1.;

4. A process for the preparation of the altered L-phenylalanyl-tRNA synthetase;

5. The use of the altered L-phenylalanyl-tRNA synthetase for the in vivo incorporation of non-proteinogenous amino acids into peptides or proteins;

The invention is described in detail hereinafter. It is furthermore defined by the contents of the claims.

All the genetic engineering operations were carried out in accordance with the procedures indicated in J. Sambrook et al. (Molecular Cloning, Cold Spring Harbor Laboratory, 1989).

Genetic engineering modifications of the L-phenylalanyl-tRNA synthetase genes (PheRS genes) from microorganisms:

The cloning of the genes which code for the $\alpha$ subunit of L-phenylalanyl-tRNA synthetase from the following microorganisms has already been described: E. coli K12 (G. Fayat et al., 1983, J Mol Biol 171, 239–261), Salmonella typhimurium and Thermus thermophilus (P. Kast, 1991, Doctoral Thesis ETH Zürich, ETH No. 9468), Bacillus subtilis (A. A. Brakhage etal., 1990, Biochimie 72, 725–734; —Erratum, 1991, Biochimie 73, 127) and yeast (mitochondria) [T. J. Koerner etal., 1987, J Biol Chem 262, 3690–3696].

The isolated synthetase genes described, or oligodeoxynucleotides derived therefrom., can be employed as probes in the DNA hybridization for isolation and cloning of synthetase genes from other microorganisms.

A modification at the DNA level, generated by genetic engineering, results in alteration of the conserved alanine residue (*) in the sequence (SEQ. ID NOS: 1–4) Gly, Phe|Trp, Ala*, Phe, Gly, Met|Leu, Gly of the: L-phenylalanyl-tRNA syntherase gene into glycine.

Within this conserved sequence there is found to be, depending on the species, either a phenylalanine or tryptophan residue ( Phe|Trp ) or a methionine or a leucine residue (Met|Leu).

It is possible to employ for the targeted genetic engineering modification which eventually results in replacement of the alanine residue by a glycine residue various methods known to the person skilled in the art (J. Sambrook et al., 1989). The method of K. L. Nakamaye et al., 1986, Nucl Acids Res 14, pages 9679–9698, is preferably used. For this, the isolated L-phenylalanyl-tRNA synthetase gene is recloned into a suitable vector from which the single-stranded DNA can be prepared (for example pBluescript® KS(+) vector, pBLS, Stratagene, Heidelberg, Germany). The orientation of the synthetase gene cloned into these vectors is chosen so that the oligodeoxynucleotides listed below bind to the single-stranded DNA formed in each case.

The single-stranded DNA of the plasmid which contains the synthetase gene is prepared in a host strain (for example E. coli TG1, Amersham Buchler, Braunschweig, Germany) by superinfection with helper phages (for example VCSM13, Stratagene, Heidelberg, Germany) and employed for the mutagenesis with one or more of the synthetic 20mer oligodeoxynucleotides (SEQ ID NOS:5–9) indicated below for a micro-organism:

| | | |
|---|---|---|
| 1. E. coli K12: | 5' CTGGTTTCGGCTTCGGGATG 3' and/or | |
| | 5' CTGGTTTCGGTTTCGGGATG 3' and/or | |
| | 5' CTGGTTTCGGATTCGGGATG 3' and/or | |
| | 5' CTGGTTTCGGGTTCGGGATG 3' | |
| 2. Salmonella typhi- murium: | 5' CTGGCTTCGGTTTTGGTATG 3' and/or | |
| | 5' CTGGCTTCGGCTTTGGTATG 3' and/or | |
| | 5' CTGGCTTCGGATTTGGTATG 3' and/or | |
| | 5' CTGGCTTCGGGTTTGGTATG 3' | |
| 3. Bacillus subtilis: | 5' AGGGCTTCGGATTCGGAATG 3' and/or | |
| | 5' AGGGCTTCGGTTTCGGAATG 3' and/or | |
| | 5' AGGGCTTCGGCTTCGGAATG 3' and/or | |
| | 5' AGGGCTTCGGGTTCGGAATG 3' | |
| 4. Thermus thermo- philus: | 5' ACGGCTTCGGCTTCGGGCTC 3' and/or | |
| | = ACGGCTTCGGATTCGGGCTC 3' and/or | |
| | 5' ACGGCTTCGGTTTCGGGCTC 3' and/or | |
| | 5' ACGGCTTCGGGTTCGGGCTC 3' | |
| 5. Yeast mito- chondria: | 5' TTGGGTGGGGATTTGGCTTG 3' and/or | |
| | 5' TTGGGTGGGGATTTGGCTTG 3' and/or | |
| | 5' TTGGGTGGGGCTTTGGCTTG 3' and/or | |
| | 5' TTGGGTGGGGGTTTGGCTTG 3' | |

Oligodeoxynucleotides are synthesized by the phosphoramidite method (for example using an Applied Biosystems model 380B DNA synthesizer).

DNA sequencing, for example by the method of F. Sanger et al. (1977), is used to check whether the replacement of the alanine codon by a glycine codon in the L-phenyl-alanyl-tRNA synthetase gene has taken place.

Resulting altered synthetase genes are integrated by homologous recombination into the chromosome of a bacterial strain [B. R. Bochner etal. (1980), J Bacteriol 143, pages 926–933 and S. C. Winans et al. (1985), J Bacteriol 161, pages 1219–1221] or recloned into a vector (for example pHE3 from the recombinant E. coli K12 strains DSM4416 and ATCC37161), and employed for the in vivo incorporation of non-proteinogenous amino acids into peptides or proteins (target peptides or proteins). E. coli strains which contain the plasmid pHE3 are sensitive to p-F-L-phenylalanine.

Recombinant means that a bacterial or yeast strain contains one or more plasmids. L-Phenylalanine halogenated in the para position, and derivatives thereof, are defined as non-proteinogenous amino acids. The halogenation can be effected by the substituents chlorine, fluorine, bromine or iodine.

Use of the L-phenylalanyl-tRNA synthetase altered by genetic engineering for the in vivo incorporation of non-proteinogenous amino acids into peptides or proteins:

Microorganisms are employed as host cells, preferably E. coli K12, for the in vivo incorporation of non-proteinogenous amino acids, preferably L-phenylalanine which is halogenated in the para position, or derivatives thereof, for example 3,4-di-F-L-phenylalanine, p-F-L-phenylalanine, p-Cl-L-phenylalanine, p.-Br-L-phenylalanine, p-I-L-phenylalanine, into peptides or proteins [S. Josephson et al. (1988), Trends Biotechnol. 6, pages 218–224] such as, for example, into hirudin (EP 17 1024), into minipro-insulin (EP 034778) and into hirudin derivatives (EP 44 8093), into colony stimulating factors such as, for example, h-GM-CSF (EP 228018), into interferons α (EP 164069) and γ (EP 427633), into human fibroblast interferon (GB 2069 504) and human leukocyte interferon (EP 34307), and into interleukin-2 (EP 163249) and herring calcitonin I (EP 261552). E. coli K12 HB101 (ATCC33694) or E. coli K12 RR28 (ATCC35111 or DSM4415) is very preferably employed.

The host cell must always contain the altered L-phenylalanyl-tRNA synthetase gene and the target gene which codes for a target peptide or protein. The altered synthetase gene pheS-Gly294 from E. coli K12 and the inducible target gene are preferably employed in a host strain, very preferably the miniproinsulin fusion protein gene which is inducible by IPTG (isopropyl β-thiogalacto-side) in E. coli K12. It is also possible to use genes of other target proteins such as, for example, of hirudin (EP 17 1024), of miniproinsulin (EP 034778), of the hirudin derivatives (EP 44 8093), the gene of colony stimulating factors such as, for example, h-GM-CSF (EP 228018), of interferons α (EP 164069) and γ (EP 427633), of human fibroblast interferon (GB 2069 504) and of human leukocyte interferon (EP 34307), and of interleukin-2 (EP 163249) and herring calcitonin I (EP 261552). The preparation of the miniproinsulin fusion protein gene is described in European Patent No. 034778.

The altered synthetase gene can be present in the chromosome or on a plasmid in the host cell. The altered synthetase gene is preferably located on the plasmid pHE3 from the recombinant E. coli K12 strains DSM4416 or ATCC37161. For this purpose, the wt synthetase gene (wt =wild type) located on the plasmid pHE3 is replaced by the altered synthetase gene using methods known to the person skilled in the art.

Preferably used for the in vivo incorporation of non-proteinogenous amino acids into proteins or peptides is an E. coli K12 host strain which contains the altered L-phenylalanyl-tRNA synthetase gene on a first plasmid (for example pHE3 from E. coli DSM4416 or ATCC37161, see above) and has the cloned, inducible target gene on a second plasmid which is compatible with the first plasmid. The two plasmids are compatible and have two different resistance genes, preferably chloramphenicol-and ampicillin-resistance genes.

The microorganisms described above, preferably E. coli K12 HB101 (ATCC33694), are shaken in minimal medium which has been mixed with glucose, tyrosine, tryptophan, thiamine and the suitable antibiotics (for example chloramphenicol and ampicillin) and with the required amino acids (for example L-proline and L-leucine) at 37° C. When the late exponential phase is reached one or more of the non-proteinogenous amino acids and IPTG (isopropyl β-thiogalactoside) as inducer are added, and the microorganisms are shaken at 37° C. for a further 3–6 hours. The fusion protein which is produced inside the cells and which contains non-proteinogenous amino-acid residues can be isolated by conventional processes, and the target protein can be obtained by known working-up methods.

For optimization of the incorporation of the non-proteinogenous amino acid into the target protein it is also possible for other control sequences to be employed and combined with various regulation systems.

For example, transcription of the target gene located on a plasmid (for example pUC18, Boehringer Mannheim, Germany) can take place by the T7 promoter [for example from plasmid pTZ18R or pTZMR, Pharmacia LKB Biotechnology, Uppsala, Sweden). Transcription can additionally be regulated by two lac operator elements arranged in tandem [for example from plasmid pYEJ001; Pharmacia LKB Biotechnology] and an antisense RNA controlled by the lambda promoter-operator system (for example from plasmid pPl-lambda, supplied by Pharmacia LKB Biotechnology). Transcription of the antisense RNA is terminated by a synthetic or natural terminator (synth.: for example trp transcriptional terminator; natural: for example rrn $BT_1T_2$ terminator from plasmid pKK223–3; Pharmacia LKB Biotechnology).

The $lacI^q$ repressor gene is isolated, for example, from the plasmid pGEX-2T (Pharmacia LKB Biotechnology) or from the plasmid pIK10 [European Patent Application No. 034 778].

The lambda $cI^{ts}$ repressor gene which is important for the transcription of the antisense RNA [T. Tsurimoto et al. (1982), Mol GenGenet 187, pages 79–86] can be located on a second, compatible plasmid such as, for example, pHE3 from E. coli ATCC37161 or DSM4416. This simultaneously controls the transcription of the terminator/antiterminator element located on the same plasmid (for example nutL,N, $t_{L1}$ from plasmid pPL-lambda; supplied by Pharmacia LKB Biotechnology) and of the T7 RNA polymerase gene [B. A. Moffatt et al. (1984), J Mol Biol 173, pages 265–269; S. Tabor et al. (1985) Proc Natl Acad Sci USA, 82, pages 1074–1078; F. W. Studlet (1990) Methods Enzymol 185, pages 60–89] with the aid of the upstream lambda promoter-operator system ($O_LP_L$). A terminator (for example rrnBT$_1$T$_2$ terminator from plasmid pKK223–3, Pharmacia LKB Biotechnology) is upstream of this $O_LP_L$ system.

The L-phenylalanyl-tRNA synthetase gene which has been altered at the DNA level can be present on the chromosome or on the second plasmid for the in vivo incorporation of non-proteinogenous amino acids (for example p-F-L-Phe or p-Cl-L-Phe).

If the altered synthetase gene (pheS-Gly294) is present on a plasmid, the host strain can have a chromosomally encoded, temperature-sensitive (L. Eidlic et al. (1965) J Bacteriol 89, pages 706–711; M. Comer et al. (1976) J Bacteriol 127, pages 923–932) or natural (wt), or p-F-L-phenylalanine-resistant L-phenylalanyl-tRNA synthetase.

It is furthermore possible to increase the incorporation of non-proteinogenous amino acids into the target protein by mutations in genes which code for the biosynthesis of L-phenylalanine (for example pheA). The E. coli K12 strain RR28 ATCC35111 (p-F-L-Phe-resistant) can be employed as host for the two plasmids (plasmid with altered pheS gene and plasmid with inducible target gene) in place of the E. coli K12 strain HB101 ATCC33694. This permits the recombinant E. coli strain to be cultured even in the presence of the substrate analog p-F-L-phenylalanine as long as the expression of the altered pheS gene on one of the abovementioned plasmids is prevented by repression. Mutations in genes for homologous recombination (for example recA gene) and the bacterial restriction system (for example hsdR gene) favor the preparation and stability of recombinant E. coli K12 strains. The stability of the target protein can be increased by mutations in genes for bacterial protease systems (lon, clpA, dnaJ, ompT and rpoH genes).

The first and second plasmid can be employed in an E. coli K12 host strain for the incorporation of the non-proteinogenous amino acids into peptides or proteins. The result is a recombinant E. coli strain. If the recombinant strain contains temperature-sensitive genes such as, for example, $pheA^{ts}$, $pheS^{ts}$ or the $\lambda cI^{ts}$ repressor gene, the microorganism is cultured in minimal medium initially at 28° C. When the $OD_{550}$ is 1, the temperature is raised to 42° C. and, a few minutes later (5–40 min), an inducer (for example IPTG) for expression of the target gene and the non-proteinogenous amino acid is added.

If the expression of the target gene is carried out by a T7 promoter, 200 μg of rifampicin/ml of culture solution are additionally added when the inducer is added. This is followed by shaking at 42° C. for 3–6 hours. After this time has elapsed, the cells are harvested and the target protein is isolated.

The isolation methods are described for the target proteins which contain natural L-phenylalanine, and are to be used correspondingly for the target protein which contains one or more L-phenylalanine residues halogenated in the para position, or derivatives thereof. The isolation methods are described, for example, for the protein, to be secreted by the microorganism, hirudin (EP 448093) and the fusion proteins interferon α (EP 164069), γ (EP 427633), miniproinsulin (EP 034778), herring calcitonin I (EP 26 1552) and GM-CSF (EP 2280 18). If the recombinant strain contains no temperature-sensitive genes, the strain is cultured at 37° C., and the subsequent procedure is as indicated above.

EXAMPLE 1

Directed mutagenesis of the L-phenylalanyl-tRNA synthetase gene (pheS) of E. coli K12

The plasmid pHE3 is isolated from E. coli ATCC37161 by alkaline lysis and cesium chloride density gradient centrifugation (J. Sambrook et al. 1989). The 1138 bp DdeI/HindII fragment which contains the wild-type pheS gene from E. coli K12 is eluted from the plasmid pHE3 by electroelution from a 0.8% agarose gel (J. Sambrook et al. 1989). The two following oligodeoxynucleotides (SEQ ID NOS: 10–11) are synthesized (Applied Biosystems DNA synthesizer model 380B) and phosphorylated at the 5'-hydroxyl end with adenosine 5'-triphosphate (ATP) and polynucleotide kinase (Boehringer Mannheim, Mannheim, Germany) as described in J. Sambrook et al. (1989).

Oligodeoxynucleotide 1 (SEQ ID NO: 10): 5'GAC-CCCGGGACCAAAATGGCAAGTAAAAT-AGCCTGATGGGATAGGCTC 3'

Oligodeoxynucleotide 2 (SEQ ID NO: 11): 5'TTAGAGC-CTATCCCATCAGGCTATTTTACTTGC-CATTTTGGTCCCGGGGTC 3'

5 μg of each of the two oligodeoxynucleotides 1 and 2 (SEQ ID NOS: 10–11) are mixed, heated to 80° C. and slowly cooled by leaving to stand at room temperature.

The oligodeoxynucleotides 1 and 2 (SEQ ID NOS: 10–11) which have been hybridized in this way are ligated to the 1138 bp DdeI/HindII fragment, which has been isolated from pHE3, using T4 DNA ligase (Boehringer Mannheim, Mannheim, Germany), and then subsequently cleaved with the restriction endonucleases SmaI and HindII (Boehringer Mannheim). The resulting 1181 bp SmaI/HindII fragment which contains the wild-type pheS gene from E. coli K12 is ligated to the vector pBLS, which has been linearized with SmaI and dephosphorylated, using T4 DNA ligase. The pBluescript® KS(+) vector pBLS is described by J. M. Short et al. (1988) Nucl Acids Res 16, pages 7583–7600 and is obtained from Stratagene, Heidelberg, Germany. The ligase mixture is transformed into competent cells of the E. coli K12 strain TG1 (Amersham Buchler, Braunschweig, Germany) (J. Sambrook et al. 1989 ). The plasmid DNA of resulting ampicillin-resistant clones is isolated and treated with AatII and BamHI. Plasmids which have a 326 bp BamHI/AatII fragment are called pKSB1-W. The plasmid pKSB2-W has a 0.867 kb BamHI/AatII fragment.

For the mutagenesis, single-stranded DNA of the plasmid pKSB2-W is prepared by the method recommended by Stratagene after superinfection of the host strain TG1 with the helper phage VCSM13 which can be obtained from Stratagene, Heidelberg, Germany.

A 20mer oligodeoxynucleotide of the sequence 5'CTG-GTTTCGGCTTCGGGATG 3' (SEQ ID NO: 12) is prepared using an Applied Biosystems DNA synthesizer (model 380B) as primer for the directed mutagenesis and, after fractionation on a 12% (w/v) polyacrylamide gel, isolated from the gel.

The directed mutagenesis of the single-stranded DNA of the plasmid pKSB2-W with the isolated 20mer oligodeoxynucleotide (see above) is carried out using the in vitro mutagenesis system obtainable from Amersham Buchler, Braunschweig, Germany, by the method of K. L. Nakamaye et al. (1986) Nucl Acids Res. 14, 9679–9698 and according to the detailed protocol of Amersham Buchler.

Single-stranded DNA from the resulting E. coli TG1 clones is isolated as described above and employed for the DNA sequencing by the dideoxy method [F. Sanger et al. (1977) Proc Natl Acad Sci USA, 74, pages 5463–5467]. The M13 sequencing kit obtained from Boehringer Mannheim, Mannheim, Germany, and deoxyadenosine 5'-(α-thio)t-riphos-phate, ($^{35}$S), (1300 Ci/mmol) supplied by Du Pont de Nemours, Bad Homburg, Germany, are used for this. The primer employed for the DNA sequencing of resulting single-stranded plasmids is the synthesized 15mer oligodeoxynucleotide of the sequence 5'GCAGATTCGCTTCCG 3'(SEQ ID NO: 13). The plasmid pKSB2-M4G contains at positions 880–882 a GGC (glycine) codon in place of the GCC (alanine) codon present in the wild-type pheS gene of E. coli K12.

EXAMPLE 2

Use of the altered L-phenylalanyl-tRNA synthetase gene pheS (Gly294) for the incorporation of p-F-L-phenylalanine into the miniproinsulin fusion protein The 174 bp AatII/BstBI fragment of the plasmid pKSB2-M4G is isolated, ligated to the isolated 3964 bp AatII/BstBI fragment of the plasmid pKSB1-W and transformed into E. coli TG1. The plasmid pKSB1-M4G which has the pheS (Gly294) gene altered at position 881 is isolated from resulting ampicillin-resistant clones.

The plasmid pHE3 which contains the wild-type pheS gene cloned in pACYC184 is obtained from E. coli ATCC37161 by alkaline lysis and cesium chloride density gradient centrifugation (J. Sambrook et al. 1989). The 326 bp AatII/BamHI fragment is obtained from the plasmid pKSB1-M4G and ligated to the isolated 3760 bp AatII/BamHI fragment of the vector pHE3. The ligase mixture is transformed into competent cells of the E. coli strain K12 RR28 (ATCC35111). The plasmid pHE3-M4G is isolated from the resulting chloramphenicol-resistant clones.

The plasmid pIK10 described in European Patent Application 034 778 encodes a fusion protein which contains amino-acid residues of human interleukin-2 fused to human miniproinsulin. Miniproinsulin has an arginine residue in place of the central C peptide. The plasmids pIK10 and pHE3-M4G are transformed into competent cells of E. coli K12 HB101 ATCC33694. One resulting chloramphenicol— and ampicillin-resistant transformant (M4G) is employed for the in vivo incorporation of p-F-L-phenylalanine (Fluka Chemie, Buchs, Switzerland) into the miniproinsulin fusion protein. For this, the recombinant strain M4G which contains the two plasmids pHE3-M4G and pIK10 is cultured in minimal medium (100 mM $KH_2PO_4$, 50 mM $Na_2HPO_4$, 12 mM $(NH_4)_2SO_4$, 1 mM $MgSO_4$, 0.1 mM $CaCl_2$, 1 mM L-tryptophan, 1 mML-tyrosine, 50 μg/ml L-leucine and 50 μg/ml L-proline, 0.4% D-glucose, 5 μg/ml thiamine, 150 μg/ml ampicillin and 20 μg/ml chloramphenicol) at 37° C.

When an optical density ($OD_{550}$) of 1.0 is reached, 1 mM IPTG (isopropyl β-thiogalactoside) and 2mMp-F-L-phenylalanine (Fluka Chemie, Buchs, Switzerland) are added. After shaking at 37° C. for 3 hours, the cells are harvested, and the human insulin which contains p-F-L-phenyl-alanine residues is isolated from the formed fusion protein as described in European Patent Application 034 778.

EXAMPLE 3

Use of the altered pheS (Gly294) gene for the incorporation of p-Cl-L-phenylalanine into the miniproinsulin fusion protein The recombinant E. coli strain M4G prepared as in Example 2 is cultured in minimal medium (see Example 2) at 37° C. until the optical density ($OD_{550}$) is 1.0. Addition of 1 mM IPTG and 2 mM p-Cl-L-phenylalanine (Fluka Chemie, Buchs, Switzerland) is followed by further shaking at 37° C. for 3 hours. Human insulin which has p-Cl-L-phenylalanine residues is obtained from the formed fusion protein from the cells by the method described in EP 034778.

---

We claim:

1. An isolated and purified L-Phenylalanyl-tRNA synthetase whose conserved alanine residue (*) in the C-terminal end of the alpha subunit in the sequence Gly, Phe/Trp, Ala*, Phe, Gly, Met/Leu, Gly (SEQ ID NOS: 1–4) is altered to glycine by a modification at the DNA level.

2. L-Phenylalanyl-tRNA synthetase as claimed in claim 1 that originates from bacteria and yeast *mitochondria*.

3. L-Phenylalanyl-tRNA synthetase as claimed in claim 1 that originates from *E. coli* K12, *Salmonella typhimurium*, *Thermus thermophilus*, *Bacillus subtills* and *Saccharomyces cerevisiae* (*mitochondria*).

4. A method for incorporating one or more non-proteinogenous amino acids into proteins in vivo, comprising:

(a) modifying an L-Phenylalanyl-tRNA synthetase gene by altering a conserved alanine residue (*) in the C-terminal sequence: Gly, Phe/Trp, Ala*, Phe, Gly, Met/Leu, Gly (SEQ ID NOS: 1–4) to a glycine residue in the alpha subunit by modification at the DNA level;

(b) recloning the modified L-Phenylalanyl-tRNA synthetase gene into a vector and inserting said vector into a host microorganism which also contains a gene coding for a target protein, or integrating the modified L-Phenylalanyl-tRNA synthetase gene into a chromosome of a host microorganism which also contains a gene coding for a target protein;

(c) incorporating the non-proteinogenous amino acids into said target protein by culturing the host microorganism recited in step b, after the gene coding for the target protein has been induced, and the non-proteinogenous amino acids or derivatives thereof have been added; and (d) isolating and purifying the target protein, the target protein containing the non-proteinogenous amino acid or non-proteinogenous amino acids.

\* \* \* \* \*